United States Patent

Brueggemann et al.

[11] Patent Number: 6,033,769
[45] Date of Patent: *Mar. 7, 2000

[54] BODY OF LAYERED STRUCTURE FOR ABSORBING LIQUIDS, THE PRODUCTION AND USE THEREOF

[75] Inventors: Helmut Brueggemann, Duisburg; Kurt Dahmen, Moenchengladbach; Dieter Lehwald, Cologne; Roland Theilmann, Krefeld, all of Germany

[73] Assignee: Stockhausen GmbH & Co. KG, Krefeld, Germany

[ * ] Notice: This patent is subject to a terminal disclaimer.

[21] Appl. No.: 08/894,437

[22] PCT Filed: Feb. 14, 1996

[86] PCT No.: PCT/EP96/00620

§ 371 Date: Oct. 2, 1997

§ 102(e) Date: Oct. 2, 1997

[87] PCT Pub. No.: WO96/25958

PCT Pub. Date: Aug. 29, 1996

[30] Foreign Application Priority Data

Feb. 20, 1995 [DE] Germany ............... 195 05 709

[51] Int. Cl.$^7$ ............... A61L 15/42; A61L 15/60; B32B 5/18; C08J 5/18

[52] U.S. Cl. ............ 428/305.5; 52/404.1; 138/141; 427/197; 427/244; 427/448; 428/17; 428/317.9; 428/319.3; 428/913; 604/369

[58] Field of Search ............... 428/305.5, 316.6, 428/317.9, 318.4, 17, 319.3, 913; 427/448, 449, 180, 181, 197, 244, 400; 604/367–369; 52/404.1; 138/141

[56] References Cited

U.S. PATENT DOCUMENTS 3,954,493 5/1976 Battista et al. .
4,000,028 12/1976 Hoey .
4,335,722 6/1982 Jackson .
4,798,744 1/1989 Goldstein et al. .
4,806,408 2/1989 Pierre et al. ............... 428/76
5,175,046 12/1992 Nguyen ............... 429/198
5,246,770 9/1993 Bottiglione et al. .
5,433,994 7/1995 McKinney et al. ............... 428/246
5,506,277 4/1996 Griesbach, III ............... 521/84.1
5,763,067 6/1998 Bruggemann et al. ............... 428/317.9

FOREIGN PATENT DOCUMENTS 378940 7/1990 European Pat. Off. .
0 427 129 5/1991 European Pat. Off. ............ C08J 9/30
94/25519 11/1994 WIPO .

Primary Examiner—Blaine Copenheaver
Attorney, Agent, or Firm—Evenson, McKeown, Edwards & Lenahan, P.L.L.C.

[57] ABSTRACT

The invention relates to layered bodies for absorbing water and aqueous liquids, consisting of at least one water-soluble polymer foam layer and particulate superabsorbent polymerizates, which contain the superabsorber on top of, between or underneath the foamed polymer layer in a quantitatively and/or locally predetermined and fixed sheet-like arrangement at a quantity ratio of polymer foam and superabsorber of from 1:500 to 50:1. The polymer foam may contain fillers, pigments and/or synthetic fibers. The layered bodies have increased absorptive capacity for water and aqueous liquids, particularly under load. They are produced by spreading the foam in a sheet-like fashion, applying the superabsorber at the predetermined quantity ratio, optionally using a template, and fixing it by a heat treatment. Such layered bodies are used in hygiene articles, as components in natural or artificial soils, as insulating material for pipes and lines, particularly cables, and building constructions, as liquid-absorbing and storing component in packaging materials, and as a part in clothing articles.

33 Claims, 2 Drawing Sheets

Diaper construction

FIG. 4

BODY OF LAYERED STRUCTURE FOR ABSORBING LIQUIDS, THE PRODUCTION AND USE THEREOF

The invention relates to bodies which absorb water and aqueous liquids and consist of foamed, soluble polymer layers and superabsorbent polymers, a production process for said bodies and their use as absorbing agents, particularly in the field of hygienics for absorbing body fluids such as blood, sweat, urine and other liquid excretions. Furthermore, the invention relates to the use of said bodies as components in wound protections, in packaging and insulation means, in textiles for clothing and cleaning purposes, and the use in the field of plant cultivation and as depot material.

Today, superabsorbent polymers are used in the form of a powder. For process simplification, it is desired to employ the superabsorbers in a fixed form, i.e., to integrate them in a matrix. According to prior art, there are a number of suggested solutions, all of which, however, suffer from drawbacks.

Bodies of layered structure, which are capable of absorbing aqueous liquids, are well-known. U.S. Pat. No. 4,000,028 describes bodies made of latex foam and fluffy cellulose which, however, do not contain any superabsorbent polymerizates, so that they have a quite limited absorptive capacity for liquids.

U.S. Pat. No. 5,128,082 describes absorbent bodies which are produced using mixtures of fluffy materials and superabsorbent polymerizates, and an enclosing latex forming the exterior layer. The polymerizate ratio in these bodies is not distributed uniformly, giving rise to the well-known problems in absorption of liquids and the associated disadavantages with respect to the wearing comfort of these hygiene articles.

EP 212,618 B1 describes diaper constructions wherein, in order to avoid these drawbacks, polymerizates having a specific grain size distribution are distributed in a layer of cellulose fibers, using a gradient. However, such constructions are not sufficiently stable; in particular, the distribution of the materials is altered during transportation.

Mixing superabsorbent polymerizates with polymeric foams containing water normally results in foam breakdown with dehydration, the open-cell structure being destroyed, so that subsequently, only SAP particles located at the surface are capable of absorbing liquids immediately. The remaining SAP particles can bind water only in a delayed fashion after the surrounding water-soluble polymer layer has dissolved.

According to EP 427,219 A2, mixtures of superabsorbent polymers and latex foams are known, which are obtained by incorporating the polymerizates as a powder spray in the foamed latex. This procedure does not permit a defined structure of those bodies; in particular, accurate distribution of the polymerizates is not possible.

The use of a tape as a component of the insulation of electric cables is known from EP 577,233 A1, which tape consists of a layer of nonwovens and a layer of foamed material and contains particles of a swelling powder affixed within the region of the layer of nonwovens.

The U.S. Pat. No. 4,649,164 describes water-absorbing foamed materials produced frbm $CO_2$-liberating foaming agents and acrylate-(meth)acrylic acid latices, the foamed latex itself constituting the absorbing material. As a resuit of the hydrophobic character of the acrylate component, the absorptive capacity of these foams is limited compared to the well-known superabsorbers.

Likewise, biocompatible open-cell polyurethane foams having guar gum as an incorporated hydrogel, which may be used as wound protections, are known from DE 4,242,015 A1, the gel component being introduced by foaming in situ during production. The water-absorbing capacity of these products is said to be limited to a value below three times the initial weight.

EP 340,945 A1 describes mixtures of elastomers and cationic water-swellable hydrocolloids, preferably chitosan salts, for use as wound protections, which have absorption values of at least 180 wt.-%, wherein the colloid particles are randomly integrated in the elastomer, and the absorptive capacity for aqueous liquids likewise is low.

Similarly, hydrophilic polyurethane foam gels are known from DE 4,233,289 A1, which are produced from mixtures of polyols, diisocyanates and superabsorbent polymerizates, the superabsorbent polymerizate being uniformly bound in the foam as a result of mixing involved in the production. The products are employed as wound dressings having defined adhesive behavior.

EP 547,474 A1 describes a process for producing absorbent materials having superabsorbent polymers distributed therein. The absorbent materials thus obtained have an absorptive capacity which is lower than the ratio of SAP incorporated in these materials would suggest, i.e., part of the SAP is blocked as a result of the selection of materials used and the production process employed. Moreover, the type of matrix material used is limited in that the melting point of this material must be above the decomposition temperature of the SAP.

EP 303,445 A1 describes an absorbent sheet material wherein a water-containing SAP has been fixed on a support. The use of this structure is confined to a patch serving as a drug reservoir.

JP Appl. No. 75-85462 describes a method for producing superabsorbent sheets made of a water-absorbing material consisting of a starch/graft polymer and being integrated in a water-soluble, film-forming polymer. As an indispensable component, the invention mentions a material as third component, which serves as base material. The superabsorbent polymer is fixed together with the soluble, film-forming polymer onto said base material.

EP 604,730 A1 describes structures containing SAP, which decompose in water. In addition to the SAP, dispersible polymers and plasticizers are mentioned as indispensable components. Said structures do not meet the requirement of a well-defined arrangement of a superabsorber in a matrix, because the methods described in this specification, such as extruding, mixing or blending, are completely unsuitable for this purpose. After disintegration of the described sheet materials, particles also remain in addition to the superabsorber; thus, the described matrix material is not water-soluble.

Therefore, it was the object to provide a body based on layer-like constructed absorbent materials for water and aqueous liquids, which avoids the above-illustrated drawbacks, i.e., which, in particular, allows absorption of water and aqueous liquids by the superabsorber, which is not hindered by the structure, shows a rapid absorption rate, allows a defined arrangement of the superabsorbent polymer within the body, is technically easy to produce, and can be used for various purposes due to its mechanical stability and flexibility.

Said object was attained by means of a layered body made of at least one water-soluble polymer foam layer and at least one layer constituted by a particulate superabsorbent polymerizate, said layered body containing the amount of superabsorbent polymerizate at a specific distribution, fixed at the foam layer interface.

In constructions having multiple layers of foam and superabsorbent polymerizate, those bodies may also be obtained which have both a defined distribution of superabsorber in each single sheet and a defined distribution of the superabsorbent polymer (e.g., a gradient) across the individual layers.

Accordingly, the invention is directed to a layered body for absorbing water and aqueous liquids, consisting of one or more water-soluble polymer foam layers and particulate superabsorbent polymerizates, which is characterized in that the superabsorbent polymerizate is contained directly on top of, between or underneath the foamed, water-soluble polymer layers in a quantitatively and/or locally predetermined and fixed sheet-like arrangement, and the quantity ratio of foamed, water-soluble polymers and superabsorbent polymerizate is from 1:1,000 to 100:1 or from 1:500 to 50:1, preferably from 1:50 to 25:1, and particularly preferred, from 1:25 to 10:1. The layered absorbent body may be rigid or flexible.

Surprisingly, despite the direct contact between the foamed, water-soluble polymers and the superabsorbent polymer, the swelling capacity of the superabsorbent polymerizate remains unimpaired during the absorption process using the layered body of the invention, while the swelling rate of the superabsorbent polymer can be determined using both type and degree of matrix material foaming.

When using a 0.9%, NaCl solution, the layered absorbent body according to the invention preferably has a retention of at least 0.1 l/m$^2$ surface area, an absorption of at least 0.1 l/m$^2$ surface area, and an absorption under load (AUL) of at least 2 g/g at 0.021 Pa.

The invention is also directed to a production process and the use of the layered absorbent body of the invention. The production process is characterized in that a) the foam of at least one water-soluble polymer having a weight per liter of from 10 to 1,000 g/l is prepared, and the foam is spread in a sheet-like fashion at a layer thickness of from 1 $\mu$m to 100,000 $\mu$m, preferably from 10 $\mu$m to 10,000 $\mu$m, and particularly preferred, from 200 $\mu$m to 5,000 $\mu$m, b) the superabsorbent particulate polymerizate at a quantity ratio of foamed, water-soluble polymer layer and superabsorbent polymerizate of from 1:1,000 to 100:1 or 1:500 to 50:1, preferably from 1:50 to 25:1, and particularly preferred, from 1:5 to 10:1, is applied at a specific distribution with respect to quantity and area to the foam spread in sheet-like fashion, optionally using at least one template, one perforated disk and/or a screen, optionally fixed by a heat treatment, the processing steps a) and/or b) optionally being repeated in any order and finally, a heat treatment is effected, optionally with slight crosslinking of the foamed layers.

As a basis for the foamed, water-soluble polymer layer, both synthetic, water-soluble polymers such as polyvinyl alcohols, poly(alkyl allyl ethers), polyglycol ethers, polyvinylpyrrolidones, polyacrylates, polymethacrylates as well as derivatives and copolymers thereof, and natural, water-soluble polymers such as guar, alginates, agar-agar, xanthan, pectin, starch or the like, as well as chemically modified raw materials such as ethers and/or esters and/or hydrolyzates and/or oxidation products of polysaccharides or proteins such as cellulose, amylose, starch or wheat bran are possible, as are copolymerizates and/or graft polymerizates based on natural or synthetic polymers.

Not least, the selection of the matrix material depends on the intended purpose of use. As a result of the optionally possible combination of natural polymers both in the matrix component and in the SAP component, a way of producing easily biodegradable absorbent bodies presents itself. Due to the matrix material, the flexibility of the superabsorbent sheet may be varied within a broad range. In a given matrix, the flexibility and stability of the superabsorbent sheet may also be varied using additives such as 2-ethylhexanol, glycerol, phthalic esters and the like, but also by means of fillers such as chalk, pigments, fibers and the like.

Foaming the water-soluble polymer is achieved using well-known means, e.g., vigorous stirring or mixing a polymer solution with admixing of air, with foaming adjuvants being added, as a rule. optionally, expanding agents such as ammonium carbonate or azodicarbonamide, for example, may be added to the material to be foamed. Thereby, one is given the opportunity to foam the water-soluble polymers in bulk, rather than as a solution. For example, a polymer foam matrix may be produced by extrusion and sprinkled with the superabsorbent polymer while still being in the plastic state.

Moreover, subsequent to extruding and solidifying, it is also possible to slightly tackify the surface of the foam matrix made of water-soluble polymer by moistening, and then to fix the superabsorbent polymer thereon. Type and quantity of the matrix material employed determine the mechanical properties of the bodies according to the invention in well-known fashion, e.g., the degree of flexibility and the surface behavior of the constructions.

It has been established that the absorption rate of water or aqueous liquids is substantially determined by the type and the degree of foaming of the polymer foam used. Superabsorbent sheet materials having slightly or non-foamed layers of soluble polymer have a lower absorption rate for water or aqueous solutions compared to those having highly foamed layers of soluble polymer.

In addition, type and quantity as well as the distribution of additionally employed filler materials have a strong impact on the mechanical stability.

Suitable filler materials are chalks, bentonites, silica gels and silicic acid, active charcoals, pigments such as titanium dioxide and iron oxide, as well as natural and/or synthetic fiber materials such as, e.g., viscose and cotton fibers and fabrics and/or polyester and polyamide fibers, and mixtures of different fibers or equivalent fabrics. In addition, finely ground plastics are suitable. In each foam layer, the type, concentration and distribution of the filler material may be the same or different. Likewise, mixtures of different fillers may be used. A single foam layer may have a filling level of from 0 to 1,000 wt.-%, relative to the amount of water-soluble polymer, preferably 400 wt.-%, at maximum, and particularly preferred, 200 wt.-% at maximum. Moreover, the described filler materials may also be incorporated in the absorbent body as a separate layer. The superabsorbent polymerizate may also be applied as a mixture with the materials mentioned as fillers.

The polymer foam may be produced in geometrically different forms, the production of a sheet-like foam layer (of any thickness) being preferred. Here, as indicated in U.S. Pat. No. 4,000,028, removable sheets of auxiliary supports, such as metal tapes and foils, silicone paper, glass fibers, glass sheets or textile fabrics may be used alternatively, or, according to the invention, sheets of materials, such as liquid-permeable and impermeable plastic films and fleeces, cellulose or paper layers or textile fabrics, which become constituents of the absorbent bodies, may be used as basis in the production.

According to the invention, the particulate, superabsorbent polymerizates may consist of water-insoluble, water-swellable polymerizates or copolymerizates of monomeric units of (meth)acrylic acid, maleic acid, itaconic acid and anhydrides and salts thereof, fumaric acid and salts thereof, particularly the alkali, alkaline earth and ammonium salts thereof, (meth)acrylamide, (meth)acrylonitrile and vinyl acetate and hydrolysis products thereof, vinylpyrrolidone, vinylpyridine, vinylsulfonic acid and esters and amides thereof, and of N-alkyl and N,N-dialkyl-substituted esters and/or amides of (meth)acrylic acid and salts thereof and/or quaternary ammonium compounds thereof. Likewise, natural water-swellable polymerizates such as carboxymethylcellulose, hydroxyethylcellulose, hydroxypropylcellulose, methylcellulose, guar seed meal, xanthans, alginates, starch and derivatives thereof, as well as graft polymerizates of these substances and the indicated monomers or mixtures of the above-mentioned polymerizates with these substances may be used.

The particulate superabsorbent polymerizate is applied to the previously prepared surface of the water-soluble polymer foam layer in a distributed form as a powder having a grain size distribution of from 1 μm to 20,000 μm.

For example, this may be effected by sprinkling the powder from suitable containers or by means of suitable devices.

The grain size of the powders depends on the use of the absorbent bodies. In the field of hygienics, powders having a grain size between 50 μm and 1,000 μm are preferred, while a range below 400 μm is selected for cable insulation use.

The finest grain fractions of the superabsorbent polymer are also fixed in the bodies of the invention, so that dust problems in subsequent use or processing are eliminated. Apart from dust formation, these finest grain fractions normally give also rise to the so-called "unblocking" during liquid absorption in conventional powder processing/application, where the finest fractions agglomerate to form a layer which impedes the transport of liquid. These problems are avoided by the foam bodies of the invention.

In a special embodiment, amount and distribution of the powder relative to a unit area may be such that only specific surface regions of the foam layer are covered, and/or the areas are covered by varying amounts. Here, application may be effected using templates, perforated disks, screens or suitable combinations thereof, optionally with classification of the particle size of the polymerizates. For example, by applying powders in the form of fine grains, a liquid blocking layer may be obtained, or, vice versa, improved distribution of liquid may be achieved by applying coarse-grained polymerizate fractions.

Amount, grain size and distribution of the particulate, superabsorbent polymerizate on the individual foamed, water-soluble polymer layers may vary.

The surface coverage of the polymer foam sheet ranges from 0.1 g to 500 g of particulate superabsorbent polymerizate, relative to one m² of foamed surface area of the body, preferably from 10 to 300 g/m², and particularly preferred, from 50 to 200 g/m².

The percentage of superabsorbent polymerizate in the overall construction of the absorbent body is 5–99 wt.-%, preferably 40–97.5 wt.-%, and particularly preferred, 50–95 wt.-%.

The production of the absorbent body is performed by applying one or more water-soluble polymer foam layers in alternation with applying the particulate superabsorber onto the layer already produced. In varying application of the polymerizate particles onto or into the single layers, bodies will be produced on the whole, wherein the absorbent polymerizate is distributed at a specific gradient. Finally, to stabilize the water-soluble polymer foam layers, drying is effected at temperatures between those normally used for freeze-drying and 300° C., preferably at temperatures between 50° C. and 240° C., optionally under reduced pressure. The microwave technology or the freeze-drying technique may also be used to dry the sheet material.

In the course of production of the layered bodies, particularly in drying thereof, chemical or physical binding between the matrix material B and the absorbing component A may possibly occur. As an example of chemical binding, the esterification reaction should be mentioned here, which may occur between carboxyl and hydroxyl groups. Physical bonds result, e.g., from loop formation or entanglement of the polymer molecules at the surface region of component A or by interactions of functional groups of the polymer molecules in the components A and B.

Optionally, the body according to the invention may be subjected to a final processing using a calender and/or an embossing roller.

A preferred example of the absorbent body according to the invention is shown in FIG. 1.

The bodies of the invention may be used for absorbing water and aqueous liquids of most various types. In particular, they ar used directly or as a component or as an additive in articles in the fields of hygienics and care in diapers, tampons and incontinence articles, as well as in sanitary articles for wound dressing. Furthermore, the absorbent bodies are suitable as plant growth media storing water and aqueous solutions, for storing and transporting plants and plant parts, for insulating pipes and lines, particularly for electric and light-conducting cables, and as components of constructional elements, e.g., for insulating external walls, and as packaging means or components for merchandise, especially for foodstuffs and beverages. Furthermore, they may be worked into clothing articles for improving the wearing comfort.

The properties of the bodies of the invention, which absorb water and aqueous liquids, can be inferred from the test methods illustrated hereinbelow.

TEST METHODS

Tea Bag Test (TBT)

The TBT was performed to determine the absorptive capacity. As test solution, a 0.9% NaCl solution was used (unless otherwise stated).

A piece of material containing about 0.2 g of SAP is punched out of the absorbing sheet. This piece is weighed in a tea bag. Thereafter, the tea bag is placed in the test solution for a defined period of time. After a draining period of five minutes, the tea bag was weighed out (determination of TBT max.); subsequently, the tea bag was spin-dried in a centrifuge (commercially available spin-drier, 1,400 rpm). Thereafter, another weighing was performed (determination of TBT ret. (retention) ).

Using multiple tests employing the same material and varying immersion times, the absorption as a function of immersion time (absorption rate) of the superabsorbent sheet material for water or aqueous solutions can be determined. The absorption of liquid is calculated relative to either 1 g of sheet, 1 g of SAP employed, or 1 m² of sheet.

Absorption under Load (AUL)

In order to determine the liquid absorption capacity under pressure, the "absorption under load" was determined as described in EP-A 0,339,461.

Departing from said procedure, a circular piece of the superabsorbent body having the size of the inner diameter of the AUL crucible was used as test substance. The absorption of liquid is calculated relative to either 1 g of body, 1 g of SAP employed, or 1 m2 of body.

Figure 1:
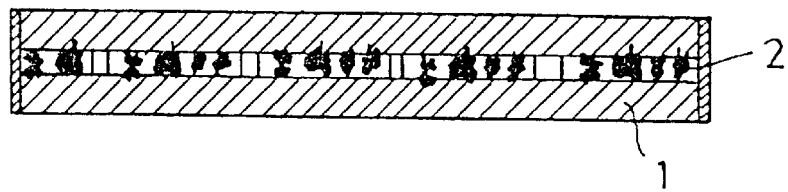
FIG. 1

View of a body according to the invention

1 Foam layer

2 Superabsorbent polymer

FIGS. 2–3

Sprinkling frame 1 (light field) permeable part of the sprinkling frame 2 (dark field) impermeable part of the sprinkling frame

FIG. 4

Diaper construction

1 Laminates of polypropylene covering fleece and polyethylene film

2 Leak protection with incorporated rubber threads

3 Covering fleece made of polypropylene

4 Polyethylene film on the back

5 Core envelope made of cellulose fibers

6 Core containing the superabsorbent body

The invention will be illustrated with reference to the following examples.

EXAMPLES 1–4

Figure 2:
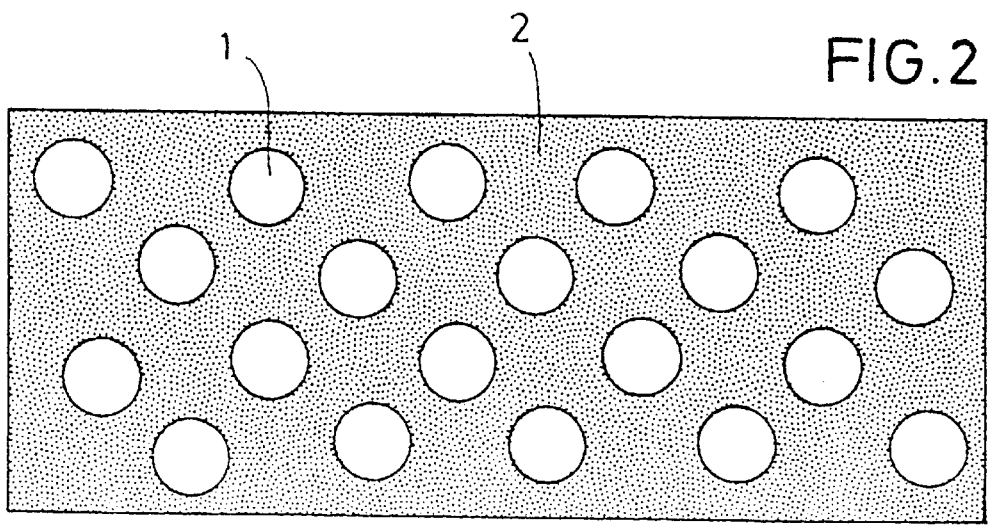

A solution is prepared from water-soluble polyvinyl cohol (6 g) and 40 g of deionized water. To this solution, 1 g of Stokal SR (35% succinamate paste) and 2 g of kyl polyglycoside are added. Using a hand mixing device, e solution is whipped up to a foam weight per liter of out 50 g/l. Part of this foam is spread uniformly on a eet (teflonized film or the like) of 400 cm². The sheet us formed is sprinkled with 12.4 g of FAVOR® SXM 100 surabsorber (slightly crosslinked, partially neutralized lyacrylate) (to this end, a template—cf., FIG. 2—is placed on the sheet) and subsequently covered with the reaining foam. Then, drying is effected for 20 minutes at a temperature of 140° C. Flexible, superabsorbent sheets are obtained, which can easily be removed from the surface (teflonized film).

TABLE 1

The table shows the dependence of the absorption rate on the type of polyvinyl alcohol used.

| Example | Type of PVA | TBT (1 min) max./ret. [g/g]/[g/g] | TBT (5 min) max./ret. [g/g]/[g/g] | TBT (30 min)* max./ret. [g/g]/[g/g] |
|---|---|---|---|---|
| 1 | Mowiol 4/88 | 13/13 | 25/20 | 50/31 |
| 2 | Mowiol 5/88 | 12/12 | 27/21 | 50/31 |
| 3 | Vinex 2144 | 16/15 | 29/24 | 50/31 |
| 4 | Vinol 205 | 15/15 | 27/22 | 50/31 |
| SXM 100 | 0 | | | 50/31 |

(The TBT values marked with * relate to the amount of superabsorber employed, the other TBT values relate to the weight per unit area)

Comparative Examples 1–4

The procedure is as in Examples 1–4, but foaming mponents is omitted. Thus, a PVA film is formed after wherein the superabsorber is integrated.

TABLE 2

The table shows the marked reduction of the absorption rate compared to Examples 1–4.

| Comparative Example | Type of PVA | TBT (1 min) max./ret. [g/g]/[g/g] | TBT (5 min) max./ret. [g/g]/[g/g] | TBT (30 min)* max./ret. [g/g]/[g/g] |
|---|---|---|---|---|
| 1 | Mowiol 4/88 | 7/7 | 17/14 | 50/31 |
| 2 | Mowiol 5/88 | 6/6 | 21/17 | 50/31 |
| 3 | Vinex 2144 | 9/9 | 22/18 | 50/31 |
| 4 | Vinol 205 | 5/5 | 15/15 | 50/31 |
| SXM 100 | 0 | | | 50/31 |

EXAMPLE 5

A solution is prepared from 1.7 g of Metylan® (commercially available wallpaper paste on the basis of methylcellulose), 2 g of alkyl polyglycoside, 2 g of Stokal® SR, 2 g of polydiol 400 and 110 g of water. Using a hand mixing device, a foam having a foam weight per liter of about 50 g/l is produced. Half of this foam is spread on a sheet of 10×40 cm. Then, sprinkling with 12.4 g of FAVOR® SXM 100 is effected (to this end, a template—cf., FIG. 2—is placed on the sheet) and subsequently covered with the second half of the foam. The sheet material is dried for 20 minutes at 140° C.

A flexible sheet material is produced, having the following absorption characteristics: TBT: max./ret. $[1/m^2]/[1/m^2]$= 15.4/9.6; AUL $(2\times10^3$ Pa$)$=9.5 $1/m^2$.

EXAMPLES 6–8

In the way described in Example 5, absorbent sheets are produced from 2 g of tylose (carboxymethylcellulose), 2 g of alkyl polyglycoside, 2 g of Stokal SR, 90 g of water, 12.4 g of Favor SXM, with addition of a plasticizer component.

Absorption characteristics of Examples 6–8: TBT: max./ret. $[1/m^2]/[1/m^2]$=15.4/9.6; AUL $(2\times10^3$ Pa$)$=9.5 $1/m^2$.

TABLE 3

The table shows the dependence of the flexibility of the sheet materials on type and amount of the plasticizers employed

| Example No. | Plasticizer | Assessment |
|---|---|---|
| 6 | Glycerol, 4.3 g | Soft, flexible, not tear-resistant |
| 7 | Glycerol, 2.0 g | Moderately flexible, breakable |
| 8 | Edenol B35[1)], 2.0 g | Scarcely flexible, breakable |

[1)]Fat epoxidate by the Henkel company

EXAMPLE 9 (a/b)

As described in the preceding examples, a foam is d from 0.2 g of guar seed meal, 50 g of water, 1 g kal SR, (a) : 3 g and (b) : 0 g of cellulose fibers, ively (softwood fibers for paper manufacturing), and of alkyl polyglycoside. As described, 12.4 g of XM 100 are incorporated in the foam and dried. In the case of (a), a stable, somewhat flexible material is obtained; in the case of (b), the sheet obtained is unstable, it cannot be handled anymore.

Absorption characteristics: TBT: max./ret. $[1/m^2]$=15.4/9.6; AUL $(2\times10^3$ Pa$)$=9.5 $1/m^2$.

EXAMPLE 10

Example 9 is repeated. However, chalk is incorporated instead of cellulose fibers. The sheet material obtained is brittle, the absorption values correspond to those measured in Example 9.

EXAMPLE 11

Figure 3:
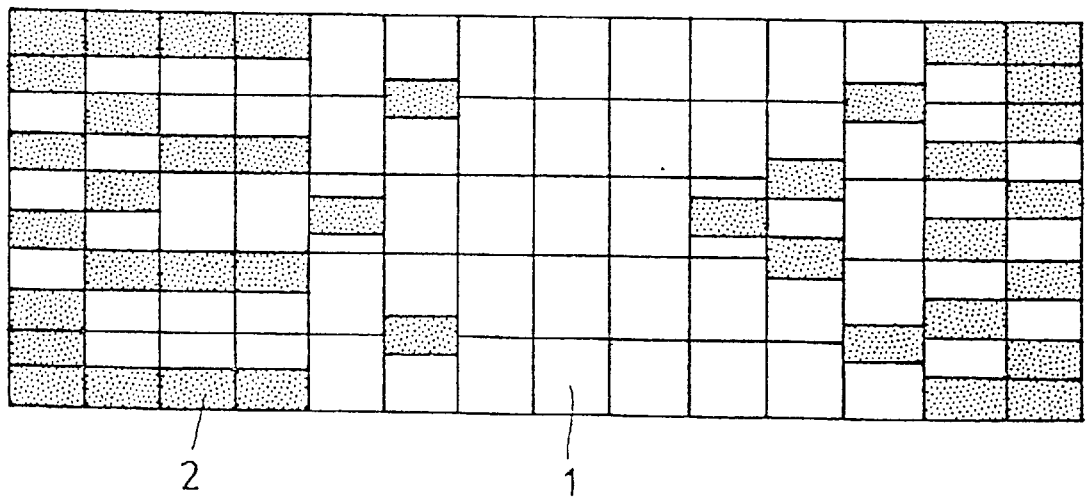

The procedure is as in Example 1; however, a template (cf., FIG. 3) is used in sprinkling the Favor. Such a template permits an arrangement of the superabsorber in the sheet-like matrix, which is preferred in the field of hygienics. The absorptive capacity of the sheet thus obtained corresponds to that of the superabsorber used.

EXAMPLE 12

Example 11 is repeated; however, only half of the water is used. The sheet thus obtained is harder and more brittle and less voluminous than that obtained according to Example 11. It has an absorptive capacity corresponding to that of the superabsorber used.

EXAMPLE 13

Figure 4:
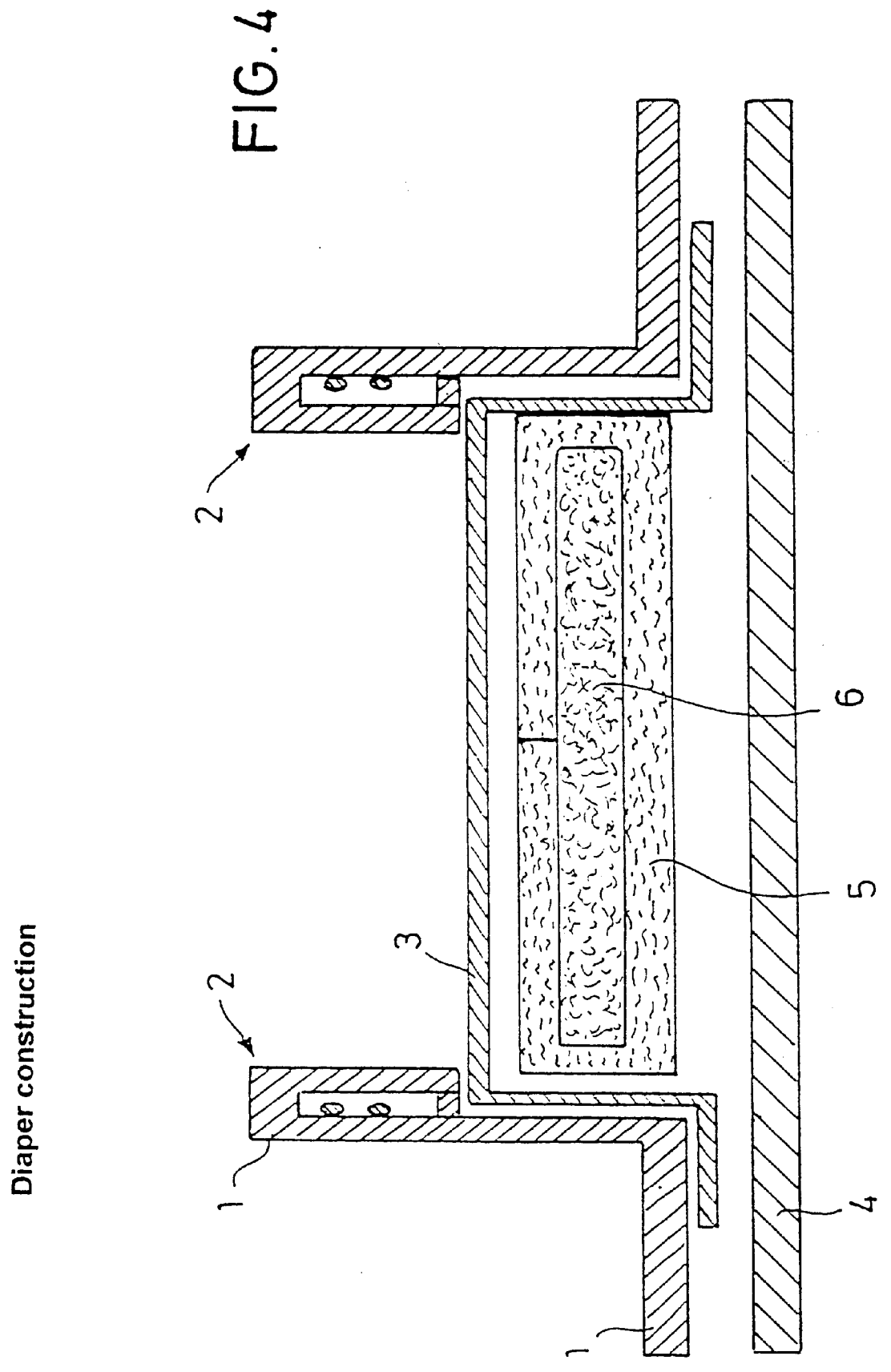

Using the sheet material produced in Example 5, a diaper is constructed according to FIG. 4. The employed PE film and the polypropylene covering fleece were used at a quality common for diaper manufacturing. The sheet produced in Example 5 is used as core.

EXAMPLE 14

10×15 cm of the sheet described in Example 2 is placed in a packaging tray and covered with a commercially available kitchen cloth (Kleenex). A deep-frozen chicken (850 g) is placed on the cloth. The entire thawed water (18 hours test period) is absorbed by the sheet according the invention.

EXAMPLE 15

Example 12 is repeated without the template, and Stockosorb® 400 (slightly crosslinked copolymer based on acrylamide) is used instead of Favor®. Strips having a size of 1×7.5 cm were cut out from this sheet. Eight of these strips were shoved completely into a cylindrical flowerpot (10 cm in height, 8.5 cm in diameter) containing soil. The soil was kept moist for 5 days. Thereafter, the film had dissolved, the SAP was situated in the soil in an arrangement suitable, e.g., for plant cultivation.

EXAMPLE 16

Example 12 is repeated without the template, and the same amount of superabsorbent depot agent formulation mentioned in Example 9 of PCT/EP93/01060 is used instead of Favor.

1 cm² of the sheet thus obtained is welded in a tea bag. The tea bag is suspended in 50 ml of a 0.2% saline solution for one hour. The saline solution is replaced after one hour.

Even after the 5th cycle, the blue coloration of the saline solution indicates release of the active substance.

We claim:

1. A layered absorbing body for water or aqueous solutions, comprising at least 2 components A and B, wherein component A is at least one particulate, superabsorbent polymer or copolymer selected from the group consisting of a synthetic polymer, a natural polymer, and combinations thereof;

wherein component B is a matrix of at least one foamed polymer or copolymer selected from the group consisting of a synthetic polymer, a natural polymer, and combinations thereof; and wherein component A is on top of, beneath, or between the component B matrix as a sheet.

2. A layered absorbing body according to claim 1, wherein component A comprises a polymer or copolymer comprising a monomer selected from the group consisting of (meth)acrylic acid, (meth)acrylo-nitrile, (meth)acrylamide, vinyl acetate, vinyl alcohol, vinylpyrrolidone, vinylpyridine, maleic acid, maleic acid anhydride, itaconic acid, itaconic acid anhydride, fumaric acid, and vinylsulfonic acid.

3. A layered absorbing body according to claim 2, wherein component A comprises a polymer or copolymer comprising an amide, an N-alkyl derivative, an N,N-dialkyl derivative or an ester of said monomer.

4. A layered absorbing body according to claim 2, wherein component A is a mixture of two or more polymers or copolymers.

5. A layered absorbing body according to claim 1, wherein component A is a crosslinked, natural polymer selected from the group consisting of guar seed meal, carboxymethylcellulose, xanthan, alginates, gum arabic, chitin, chitosan, agar-agar, hydroxyethylcellulose, hydroxypropylcellulose, methylcellulose, starch, starch derivatives and mixtures of said polymers.

6. A layered absorbing body according to claim 1, wherein component B comprises a water-soluble polymer or copolymer comprising a monomer selected from the group consisting of (meth)acrylic acid, (meth)acrylonitrile, (meth)acrylamide, vinyl acetate, vinyl alcohol, vinylpyrrolidone, vinylpyridine, maleic acid, maleic acid anhydride, itaconic acid, itaconic acid anhydride, fumaric acid, and vinylsulfonic acid.

7. A layered absorbing body according to claim 6, wherein component B comprises an amide, an N-alkyl derivative, an N,N-dialkyl derivative or an ester of said monomer.

8. A layered absorbing body according to claim 6, wherein that component B is a mixture of polymers or copolymers.

9. A layered absorbing body according to claim 1, wherein component B is a soluble, natural polymer selected from the group consisting of carboxymethylcellulose, xanthan, alginates, gum arabic, chitin, chitosan, agar-agar, hydroxyethylcellulose, hydroxypropylcellulose, methylcellulose, starch, starch derivatives and mixtures thereof.

10. A layered absorbing body according to claim 1, wherein component B has a foam weight per liter of between 10 g/l and 1,500 g/l.

11. A layered absorbing body of claim 10, wherein said foam weight per liter is between 25 g/l and 850 g/l.

12. A layered absorbing body according to claim 10, wherein said foam weight per liter is between 50 g/l and 500 g/l.

13. A layered absorbing body according to claim 1, wherein a ratio B:A is between 1:500 and 50:1.

14. A layered absorbing body according to claim 13, wherein said ratio B:A is between 1:50 and 25:1.

15. A layered absorbing body according to claim 13, wherein said ratio B:A is between 1:25 and 10:1.

16. A layered absorbing body according to claim 1, wherein the components A and B have chemically reacted with each other.

17. A layered absorbing body according to claim 1, wherein component A and component B are physically linked together.

18. A layered absorbing body according to claim 1, wherein said body is in a form selected from the group consisting of a sheet, a film, a roll, and a laminate.

19. A layered absorbing body according to claim 1, wherein said sheet is applied to the component B matrix in a local area.

20. A process for producing an absorbent body according to claim 1, comprising:

foaming a solution of component B;

applying said foam to a sheet;

sprinkling said foamed sheet with component A; and drying said sheet.

21. A process according to claim 20, further comprising repeating the applying and sprinkling a plurality of times, optionally with intermediate drying.

22. A process according to claim 20, further comprising finally treating the sheet by applying additional foam to the sheet and drying the sheet.

23. A process according to claim 20, wherein the applying is by spreading, knife coating, spraying, pouring, or lick-rolling.

24. A process according to claim 20, wherein the sprinkling is by templates, thereby permitting a defined pattern of component A on component B.

25. A hygiene article in the sanitary and medical fields comprising a layered absorbing body according to claim 1.

26. A natural or artificial soil for plant cultivation comprising a layered absorbing body according to claim 1.

27. A pipe or line comprising a layered absorbing body according to claim 1 as a water-blocking insulating material.

28. A pipe or line according to claim 27, wherein said pipe or line is an electric or light-conducting cable.

29. A building material comprising a layered absorbing body according to claim 1 as a water-blocking insulating material.

30. A building material according to claim 29, wherein said building material is an external wall.

31. A packaging material comprising a layered absorbing body according to claim 1.

32. A clothing article comprising a layered absorbing body according to claim 1.

33. A depot for the controlled release of an active substance comprising a layered absorbing body according to claim 1.

* * * * *